(12) United States Patent
Takahashi et al.

(10) Patent No.: US 8,337,952 B2
(45) Date of Patent: Dec. 25, 2012

(54) METAL SULFIDE THIN FILM AND METHOD FOR PRODUCTION THEREOF

(75) Inventors: Tadashi Takahashi, Hamamatsu (JP); Naoyuki Takahashi, Hamamatsu (JP); Takato Nakamura, Hamamatsu (JP)

(73) Assignee: Suzuki Motor Corporation (JP)

( * ) Notice: Subject to any disclaimer, the term of this patent is extended or adjusted under 35 U.S.C. 154(b) by 2523 days.

(21) Appl. No.: 10/525,443

(22) PCT Filed: Aug. 27, 2003

(86) PCT No.: PCT/JP03/10814
§ 371 (c)(1),
(2), (4) Date: Feb. 24, 2005

(87) PCT Pub. No.: WO2004/020688
PCT Pub. Date: Mar. 11, 2004

(65) Prior Publication Data
US 2006/0127692 A1    Jun. 15, 2006

(30) Foreign Application Priority Data
Aug. 30, 2002 (JP) .................................. 2002-252450

(51) Int. Cl.
*C23C 16/08* (2006.01)
(52) U.S. Cl. ........... 427/255.31; 427/248.1; 427/255.28; 427/255.29; 427/255.39
(58) Field of Classification Search ................ 427/248.1, 427/255.28, 255.31, 255.39
See application file for complete search history.

(56) References Cited

FOREIGN PATENT DOCUMENTS

| JP | 08-199333 | 8/1996 |
|---|---|---|
| JP | 08-218161 | 8/1996 |

OTHER PUBLICATIONS

Takahashi et al, Preparation of pyrite thin films by atmospheric pressure chemical vapor deposition using FeCl3 and CH3CSNH2, J. Mater. Chem., 2000, 10, p. 2346-2348.*
Schleich et al, Iron pyrite and iron marcasite thin films prepared by low pressure chemical vapor deposition, Journal of Crystal Growth, vol. 112, Issue 4, Jul. 1991, Abstract (2 pages).*
Sasaki et al, Iron pyrite thin film prepared by double source vacuum vapor deposition, Journal of Materials Science Letters 18 (1999), p. 1193-1195.*

(Continued)

*Primary Examiner* — Elizabeth Burkhart
(74) *Attorney, Agent, or Firm* — Myers Bigel Sibley & Sajovec, P.A.

(57) ABSTRACT

An object of the present invention is to provide a single-phase film of a metal sulfide with good quality, and a method for preparing a metal sulfide film at a low cost in a convenient manner. The present invention provides a preparation method of a metal sulfide film, comprising the steps of providing metal halide, such as iron halide ($FeCl_3$, $FeI_3$, $FeBr_3$, $FeCl_2$, $FeI_2$ and $FeBr_2$), as a first raw material and a thioamide compound, such as thioacetamide, as a second raw material, preferably vaporizing these raw materials and reacting them at atmospheric pressure; and a metal sulfide film prepared by this method.

6 Claims, 2 Drawing Sheets

OTHER PUBLICATIONS

Takahashi et al., "New vapor phase deposition of pyrite thin films using $FeCl_3$ and $CH_3CSNH_2$", Journal of Materials Science Letters 19:2223-2224 (2000).

Takahashi et al., "Preparation of pyrite thin films by atmospheric pressure chemical vapor deposition using $FeCl_3$ and $CH_3CSNH_2$", Journal of Materials Chemistry 10:2346-2348 (2000).

Lichtenberger et al., "Structural optical and electrical properties of polycrystalline iron pyrite layers deposited by reactive d.c. magnetron sputtering", Thin Solid Films 246:6-12 (1994).

Höpfner et al., "Stoichiometry-, phase- and orientation-controlled growth of polycrystalline pyrite (FeS2) thin films by MOCVD", Journal of Crystal Growth 151:325-334 (1995).

International Search Report corresponding to PCT/JP03/010814 mailed on Dec. 9, 2003.

International Preliminary Examination Report corresponding to PCT/JP2003/010814 filed Aug. 27, 2003.

* cited by examiner

METAL SULFIDE THIN FILM AND METHOD FOR PRODUCTION THEREOF

RELATED APPLICATION

This application claims priority under 35 U.S.C. §371 from PCT Application No. PCT/JP03/010814, filed in Japanese on Aug. 27, 2003, which claims the benefit of Japanese Patent Application Serial No. 2002-252450 filed on Aug. 30, 2002, the disclosures and contents of which are incorporated by reference herein in their entireties.

TECHNICAL FIELD

The present invention relates to a metal sulfide film and a method for preparing thereof.

BACKGROUND ART

Thin films of iron sulfide, especially, iron disulfide (pyrite $FeS_2$), are expected as a light absorbing material in film solar cells, and have been actively developed in recent years. In order to put such metal sulfide films on the market as industrial products, not only high quality but also mass productivity at a low cost is requested. Technologies satisfying such requirements have so far been developed.

Examples of a preparation method of such a metal sulfide film include film preparing methodes under vacuum such as MOCVD or sputtering, and sulfurization by the heat treatment of a metal film.

MOCVD (Metal Organic Chemical Vapor Deposition) is one of the CVD methods in which a film is formed on a substrate by reacting a raw material at high temperatures, and is particularly a method that uses an organic metal as the raw material. The film preparation method by MOCVD is, for example, disclosed in Journal of Crystal Growth, 151, p. 325, (1995).

The film preparation method by sputtering is a method of spraying an inert gas to a material such as metal and attaching molecules thus sputtered to the surface of an object, and it is disclosed, for example, in Thin Solid Films, 246, p. 6, (1994).

These preparation methodes however involve many problems upon industrialization, for example, they need expensive vacuum systems or expensive raw materials such as TBDS, a film forming rate is low, or the number of steps for the method is large. In particular, iron sulfide exists in the various forms such as troilite FeS, pyrrhotite $Fe_{1-x}S$, pyrite $FeS_2$, and marcasite $FeS_2$, and thus it is necessary to set strict conditions for the preparation of a good-quality film composed of only a single phase among these various forms. Especially, there is a considerable difficulty in preparation of a film of iron disulfide (pyrite $FeS_2$) which is expected as a material for film solar cells. Owing to the existence of a sulfur defect, the resulting film partially becomes, for example, pyrrhotite $Fe_{1-x}S$, meaning the preparation of a multiphase film.

As a preparation method of a metal sulfide film, a method is proposed in which a $Fe_2O_3+Cu_2O$ film or Fe+S film is formed, and subsequently the film is heated in a sulfur-containing atmosphere to sulfurize the metal, in Japanese Patent Application Unexamined Publication No. 8-199333/1996 A and Japanese Patent Application Unexamined Publication No. 8-218161/1996 A. This method is however complicated and needs post-treatment such as heat treatment after film formation. In addition, it is difficult to prepare a single-phase film with good quality, because strict conditions are required for completely sulfurizing the metal by heat treatment.

DISCLOSURE OF THE INVENTION

An object of the present invention is to provide a single-phase metal sulfide film with good quality, and a method for preparing the film at a low cost in a convenient manner.

With a view to attaining the above-described object, there is thus provided in the present invention a method for preparing a metal sulfide film, comprising the steps of providing metal halide as a first raw material and a thioamide compound as a second raw material. Preferably, the method comprises vaporizing the metal halide and the thioamide compound, and reacting the metal halide with the thioamide compound at atmospheric pressure.

It is preferable that the metal halide is iron halide. Especially, it is preferable that the iron halide is at least one selected from the group consisting of $FeCl_3$, $FeI_3$, $FeBr_3$, $FeCl_2$, $FeI_2$ and $FeBr_2$. It is preferable that the thioamide compound is thioacetamide ($CH_3CSNH_2$). The term "thioamide compound" as used herein means an organic compound (R—$CSNH_2$) having a thioamide group (—$CSNH_2$).

Especially, it is preferable that a triazine compound is formed as a byproduct.

In another aspect of the present invention, there is also provided a metal sulfide film prepared by the above-described preparation method.

According to the present invention, the metal halide and the thioamide compound used as raw materials are not required to be as pure as those employed in the conventional vacuum systems for film preparation. A metal sulfide film can therefore be prepared by using inexpensive raw materials. In addition, a sulfur element can be fed relatively easily by using the thioamide compound as a sulfur source. This makes it possible to efficiently sulfurize metal halide, thereby preparing a good quality metal sulfide film with less defects. Especially, as described below in detail, in the reaction step of the thioamide compound, since a triazine compound is by-produced and a sulfur element is formed as a simple substance, metal halide can be sulfurized efficiently by the resulting sulfur element, whereby a single-phase film of a metal sulfide with good quality can be prepared at a relatively low temperature.

In the method for preparing a metal sulfide film according to the present invention, a growth rate of the film is rapid, and accompanying the formation of the film, a good quality metal sulfide film can be achieved without employing, as a post-treatment step, sulfurization by heat treatment.

Moreover, a metal sulfide film can be prepared under atmospheric pressure so that the generation of defects in a sulfur element can be prevented and a good quality metal sulfide film can be prepared. In addition, the film can be prepared in a simplified system, because an expensive vacuum system is not required for its preparation.

In particular, a single-phase film of iron sulfide (pyrite $FeS_2$) which is expected as a light absorbing material of film solar cells can be prepared using iron halide and thioamide compound as raw materials.

As described later in detail, the present invention provides a single-phase film of a metal sulfide with good quality and a convenient and low-cost preparation method of a metal sulfide film. The preparation method of a metal sulfide film according to the present invention is suitable for industrialization, because a film forming rate is rapid and no expensive system such as vacuum gauge is necessary.

BEST MODE FOR CARRYING OUT THE INVENTION

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

Unless otherwise defined, all technical and scientific terms used herein have the same meaning as commonly understood by one of ordinary skill in the art to which this invention belongs.

Embodiments of a preparation method of a metal sulfide film according to the present invention will hereinafter be described, referring to accompanying drawings. It should however be borne in mind that the present invention is not limited to or by the below-described embodiments.

Figure 1:
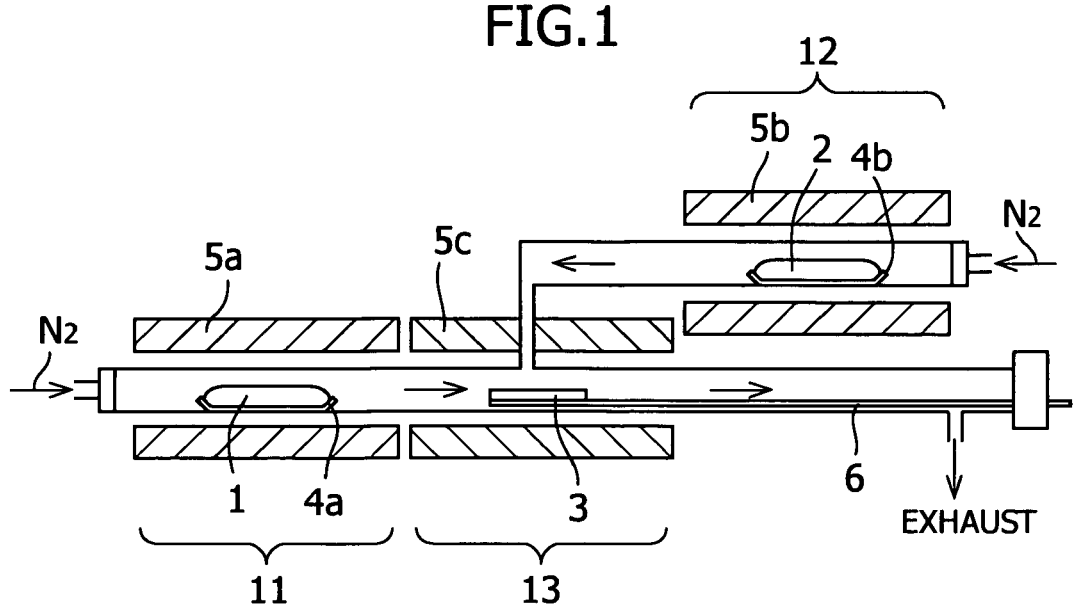
FIG. 1 is a schematic view illustrating one embodiment of an apparatus for preparing a metal sulfide film according to the present invention.

FIG. 1 illustrates one embodiment of an apparatus for carrying out the present invention. This apparatus is a horizontally placed reactor and is equipped with, as principal members, a first raw material vaporizer 11, a second raw material vaporizer 12 and a film forming section 13.

The first raw material vaporizer 11 has, at the periphery thereof, a heater 5a for controlling the first raw material vaporizer 11 to a predetermined temperature and it has, inside thereof, a raw material boat 4a for placing therein the first raw material. The first raw material vaporizer 11 is capable of being fed a carrier gas from one end thereof and to exhaust gas from the other end.

Similar to the first raw material vaporizer, the second raw material vaporizer 11 has, at the periphery thereof, a heater 5b for controlling the second raw material vaporizer 12 to a predetermined temperature and it has, inside thereof, a raw material boat 4b for placing therein the second raw material. The second raw material vaporizer 12 is capable of being fed a carrier gas from one end thereof and to exhaust gas from the other end.

The film forming section 13 has, at the periphery thereof, a heater 5c for controlling the film forming section 13 to a predetermined temperature and it has, inside thereof, a substrate support 6 for disposing the substrate 6 thereon. The gases exhausted from the first raw material vaporizer 11 and the second raw material vaporizer 12 are fed to the film forming section 13. The direction of the gases to be fed to the film forming section 13 and containing these raw materials toward the substrate 3 is not particularly limited. Specifically, the gases may be fed to the surface of the substrate 3 on which a film is to be formed either in a parallel or vertical direction or a direction having a certain angle.

Embodiment of the preparation method of a metal sulfide film according to the present invention will next be described using the apparatus of FIG. 1.

A metal halide 1 as a first raw material and a thioamide compound 2 as a second raw material are provided on the raw material boats 4a and 4b, respectively. As described above, it is preferable that the metal halide 1 is iron halide, and it is preferable that the iron halide is $FeCl_3$, $FeI_3$, $FeBr_3$, $FeCl_2$, $FeI_2$ or $FeBr_2$. $FeCl_3$ is especially suited because it can be handled easily and is inexpensive. As the thioamide compound 2, thioacetamide is preferred. The metal halide 1 and the thioamide compound 2 are not required to be as pure as materials used in conventional vacuum film preparation apparatuses and purity as high as about 99.5% is sufficient.

A portion of each raw material is vaporized by heating the first raw material vaporizer 11 and the second raw material vaporizer 12. The temperature to heat each raw material may be a temperature at which each raw material vaporizes and no particular limitation is imposed on it. For example, when $FeCl_3$ is used as the first raw material, the first raw material vaporizer 11 is preferably heated to about 180° C., and when thioacetamide is used as the second raw material, the second raw material vaporizer 12 is preferably heated to about 70° C.

The raw materials thus vaporized are then fed to the film forming section 13 by a carrier gas. The film forming section 13 in which the substrate 3 has been disposed is maintained at a predetermined temperature in advance by heating.

The film forming section 13 is preferably heated to 350 to 450° C., more preferably 375 to 425° C. At this time, the pressure in the apparatus can be maintained at an atmospheric pressure.

As the substrate 3, glass or single-crystal materials such as sapphire and silicon can be used without particular limitation. It is also possible to provide a metal sulfide film, for example, single-crystal film, with excellent crystallinity, by providing, on the substrate 3, a buffer layer for relaxing a difference in the lattice mismatch degree with a metal sulfide film, and forming the metal sulfide film on this buffer layer. The buffer layer can be formed by the ordinary film forming treatment. When an iron sulfide film is formed, for example, Fe, FeS, $Fe_{1-x}S$, $FeS_2$, $MOS_2$ or the like can be used as the buffer layer.

The raw materials heated in the film forming section 13 reacted each other, whereby a triazine compound is formed from the thioamide compound 2 and simultaneously, a metal sulfide film is formed on the substrate 3.

Amounts of the raw materials can be controlled by the heating temperature of these raw materials or a flow rate of a carrier gas. As the carrier gas, an inert gas such as argon and helium can be used, but nitrogen ($N_2$) is preferred because of its low cost.

EXAMPLES

Examples of the preparation method of a metal sulfide film according to the present invention will next be described. Based on the above-described embodiment, a horizontally placed reactor made of a quartz glass similar to that of FIG. 1 was used.

In this Example, an ion sulfide (pyrite $FeS_2$) film was prepared using $FeCl_3$ as a first raw material and thioacetamide ($CH_3CSNH_2$) as thioacetamide. As the substrate 3, a glass substrate was employed. The first raw material vaporizer 11, second raw material vaporizer 12, and film forming section 13 were heated to 180° C., 70° C. and 400 ° C., respectively. Film formation was carried out for 60 minutes, while feeding $N_2$ as a carrier gas to give a total gas flow rate of 1200 mL/min.

During the film formation, the pressure inside of the apparatus was kept at atmospheric pressure.

Figure 2:
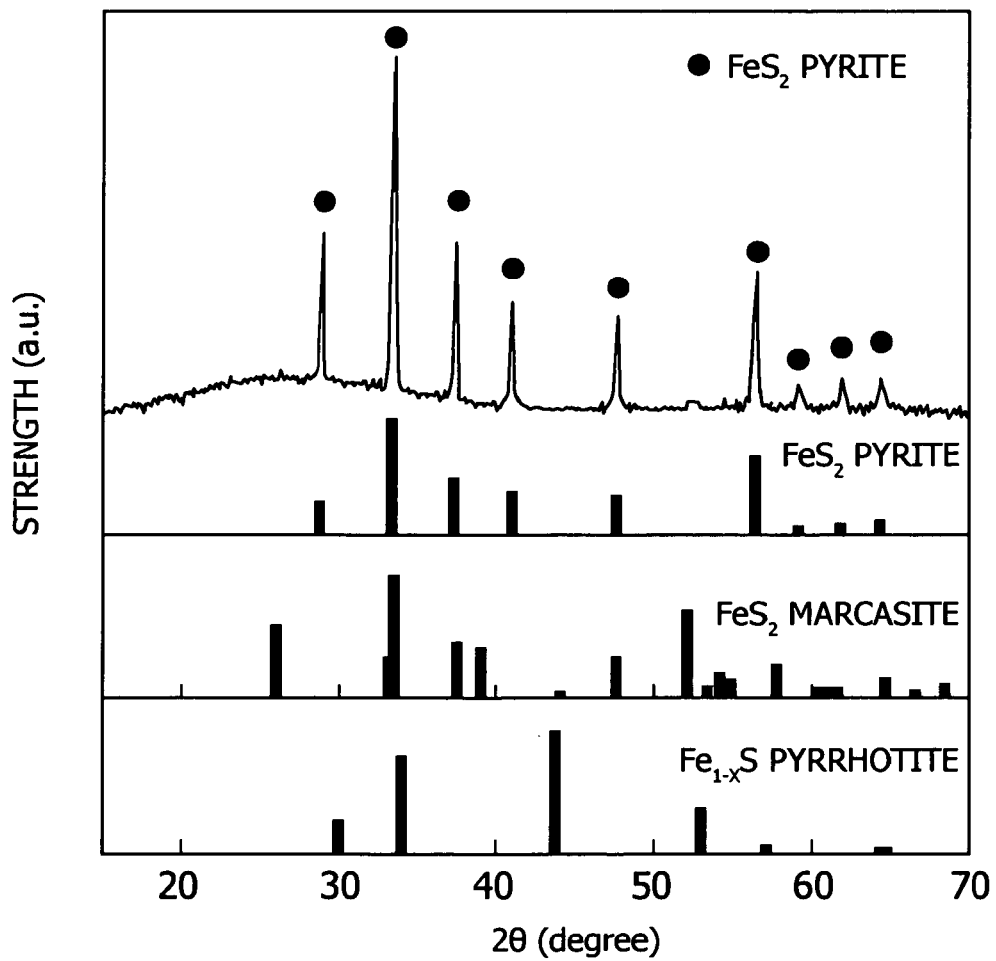
FIG. 2 is a graph illustrating the X-ray diffraction results of an iron sulfide (pyrite $FeS_2$) film prepared by the method of a metal sulfide film according to the present invention.

The result of X-ray diffraction of the film thus formed on the glass substrate, and X-ray patterns of $FeS_2$ (pyrite), $FeS_2$ (marcasite) and $Fe_{1-x}S$ (pyrrhotite) listed in the JCPDS card are shown in FIG. 2. The result suggests that a film of $FeS_2$ (pyrite) was formed, which can be used for a light absorbing material of a film solar cell. In addition, the resulting $FeS_2$ (pyrite) film is found to have no impurity therein and have no defects, being a single-phase film with good quality. It has been understood that the film preparation method of the present invention is very advantageous for industrialization, because it does not need any treatment after film formation such as heat treatment (sulfurization) in a sulfur atmosphere.

Figure 3:
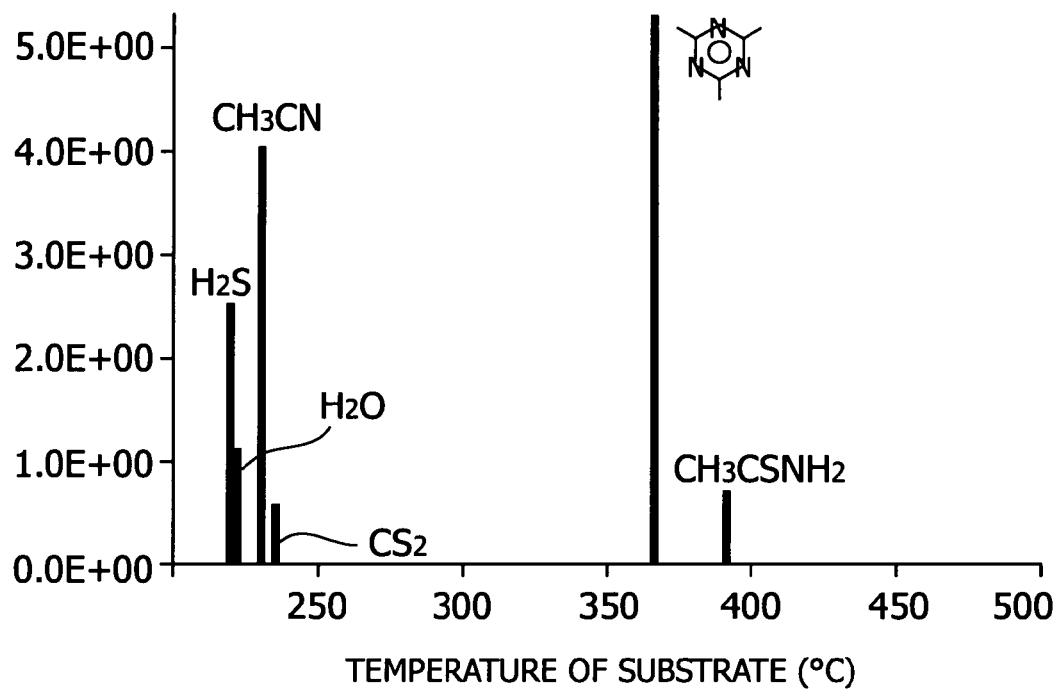
FIG. 3 is a graph illustrating the results of gas chromatograph and mass analysis of an iron sulfide (pyrite $FeS_2$) film prepared by the preparation method of a metal sulfide film according to the present invention.

Furthermore, the present inventors have revealed the reaction mechanism in this examples by using gas chromatography and mass spectroscopy in combination. FIG. 3 illustrates the analysis results, by a gas chromatograph mass spectrometer, of a substance generated upon heating of thioacetamide at a predetermined temperature. FIG. 3 suggests that trimethyltriazine was formed, which is represented by the following formula at a substrate temperature of about 368° C.

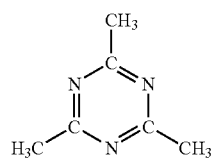

Figure 4:
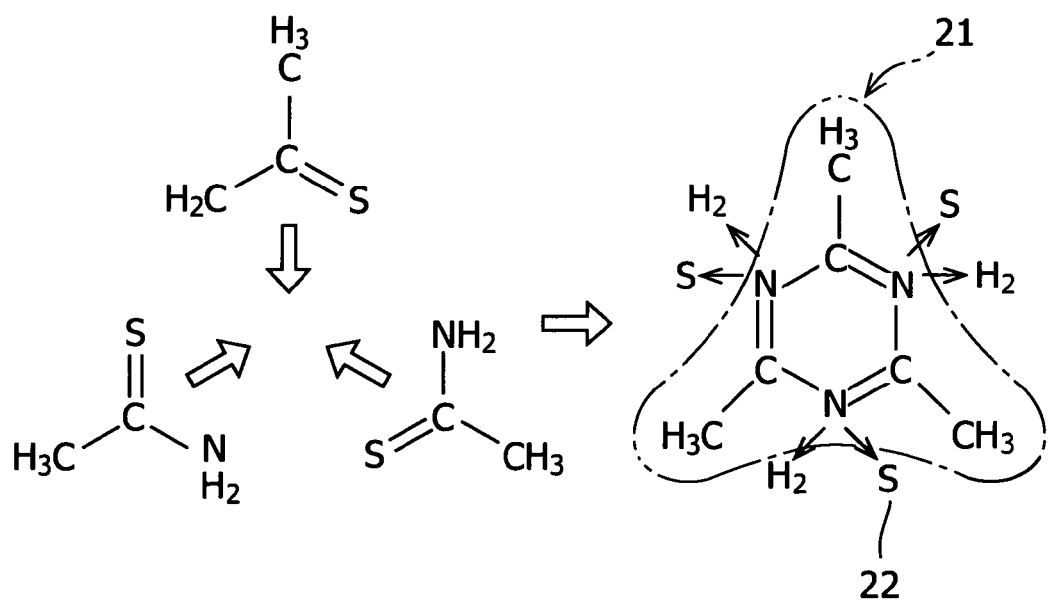
FIG. 4 is a schematic view illustrating a reaction mechanism in which trimethyltriazine is formed from thioacetamide.

As illustrated in FIG. 4, it is understood that trimethyltriazine 21 is formed from thioacetamide at around 400° C., that is, the film forming temperature of this Example.

From the above-described results, it is suggested that pyrite $FeS_2$ is formed from $FeCl_3$ and thioacetamide in accordance with the reaction mechanism represented by the following reaction scheme:

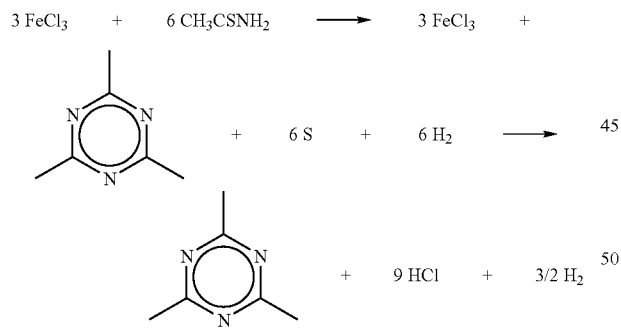

Described specifically, trimethyltriazine 21 is formed from thioacetamide under heating, accompanying formation of sulfur 22 as a simple substance. Furthermore, a single-phase film of pyrite $FeS_2$ is formed by the sulfurization of $FeCl_3$ with the sulfur 22 as a simple substrate.

As described above, during the formation of a triazine compound from a thioamide compound, sulfur as a simple substrate is formed. This sulfur contributes to the formation of a metal sulfide film, whereby a metal sulfide film with good quality can be prepared without post-treatment.

Comparative Example

The present inventors have tried to prepare a film using $FeCl_3$ as a first raw material, and a hydrogen sulfide ($H_2S$) gas or thiourea ($CH_3CSCH_3$) as a second raw material which will be a sulfur source. The hydrogen sulfide ($H_2S$) gas is generally used as a sulfur source, while thiourea ($CH_3CSCH_3$) has an analogous structure to thioacetamide. Use of either compound as a sulfur source however failed to prepare an ion sulfide film. These results suggest that use of a thioamide compound as the second raw material is important.

The invention claimed is:

1. A method for preparing a metal sulfide film, comprising the steps of providing metal halide as a first raw material and a thioamide compound as a second raw material, vaporizing the metal halide and the thioamide compound, and reacting the metal halide with the thioamide compound at atmospheric pressure in a film forming section heated to from 375 to 425° C. to form the metal sulfide film on a substrate.

2. The method for preparing an iron sulfide film according to claim 1, wherein the metal halide is iron halide and the metal sulfide film is pyrite $FeS_2$ film.

3. A method for preparing a metal sulfide film, comprising the steps of vaporizing metal halide and a thioamide compound, and reacting the metal halide with the thioamide compound in a heated film forming section to produce the metal sulfide film on a substrate as well as a triazine compound from the thioamide compound, wherein the step of reacting is performed at atmospheric pressure in the film forming section heated to from 375° C. to 425° C.

4. The method for preparing a metal sulfide film according to claim 3, wherein the thioamide compound is thioacetamide, the triazine compound is trimethyltriazine, and the step of reacting accompanies formation of sulfur as a simple substance.

5. A method for preparing a metal sulfide film according to claim 3, wherein an iron sulfide film is formed by a reaction represented by the following formula:

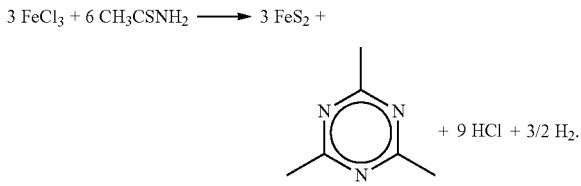

6. The method for preparing an iron sulfide film according to claim 3, wherein the metal halide is iron halide and the metal sulfide film is pyrite $FeS_2$ film.

* * * * *

UNITED STATES PATENT AND TRADEMARK OFFICE
CERTIFICATE OF CORRECTION

PATENT NO.        : 8,337,952 B2                                          Page 1 of 1
APPLICATION NO.   : 10/525443
DATED             : December 25, 2012
INVENTOR(S)       : Takahashi et al.

It is certified that error appears in the above-identified patent and that said Letters Patent is hereby corrected as shown below:

In the Specification:

Column 4, Line 8: Please correct "is $FeCl_3$, $_{FeI3}$,"
to read -- is $FeCl_3$, $FeI_3$, --

Column 5, Line 50: Please replace the scheme on line 50 below

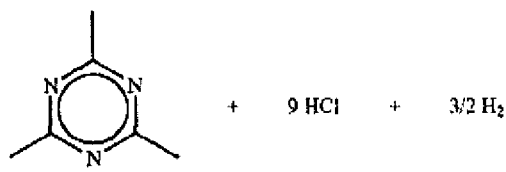

To read:

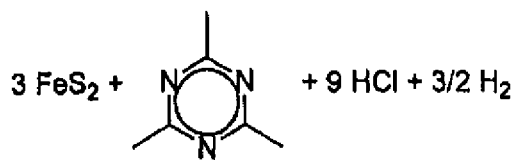

Signed and Sealed this
Fourth Day of February, 2014

Michelle K. Lee
*Deputy Director of the United States Patent and Trademark Office*